United States Patent [19]

Sherburne

[11] Patent Number: 4,869,715
[45] Date of Patent: Sep. 26, 1989

[54] ULTRASONIC CONE AND METHOD OF CONSTRUCTION

[76] Inventor: Fred S. Sherburne, 38 Deerhill Dr., Rolling Hills Estates, Calif. 90274

[21] Appl. No.: 184,431

[22] Filed: Apr. 21, 1988

[51] Int. Cl.$^4$ .......................................... A61B 17/00
[52] U.S. Cl. ...................................... 604/22; 128/305
[58] Field of Search ................ 604/22; 128/303, 305, 128/24 A, 303 C

[56] References Cited

U.S. PATENT DOCUMENTS

| | | | |
|---|---|---|---|
| 3,584,327 | 6/1971 | Murry | 128/303 C |
| 3,589,363 | 6/1971 | Banko et al. | 128/276 |
| 3,693,613 | 9/1972 | Kelman | 128/24 A |
| 3,732,858 | 3/1973 | Banko | 128/2 B |
| 3,896,811 | 7/1975 | Stoez | 128/303 C |
| 3,942,519 | 3/1976 | Shock | 128/303 C |
| 3,945,375 | 3/1976 | Banko | 128/6 |
| 4,011,869 | 3/1977 | Seiler, Jr. | 128/276 |
| 4,417,578 | 11/1983 | Banko | 604/22 |
| 4,428,748 | 1/1984 | Peyman et al. | 604/22 |
| 4,515,583 | 5/1985 | Sorich | 604/22 |
| 4,526,571 | 7/1985 | Wuchinich | 604/22 |
| 4,531,934 | 7/1985 | Kossovsky et al. | 604/22 |
| 4,589,415 | 5/1986 | Haaga | 128/328 |
| 4,609,368 | 9/1986 | Dotson, Jr. | 604/22 |

Primary Examiner—Stephen C. Pellegrino
Attorney, Agent, or Firm—Fulwider, Patton, Rieber, Lee & Utecht

[57] ABSTRACT

An ultrasonic cone and method of construction for the emulsification of cataract lenses employed in a hand-held surgical aspirator having an angle of incidence $\theta$ equal to or less than thirty degrees, the angle of incidence being located at the point of tangency of a transition radius construction line at the intersection with a horizontal line passing through a hub portion of the cone, the angle construction for eliminating the erosion of the cone along the transition radius and for minimizing the size and improving the dispersement of bubbles created by cavitation of the cone in a saline solution and migrating toward the cataract lens operative site when ultrasonic frequencies of vibration of greater than forty kilohertz and cone shaft horizontal stroke lengths exceeding four- to-five thousandths of an inch are employed. Alternative embodiments disclose an adapter apparatus for employing disposable cone shafts and an array of shaft distal ends for improving the efficiency of the ultrasonic cone.

27 Claims, 4 Drawing Sheets

ULTRASONIC CONE AND METHOD OF CONSTRUCTION

BACKGROUND OF THE INVENTION

The invention relates generally to an ultrasonic apparatus employed in eye surgery and more particularly to a new and improved ultrasonic cone and method of construction for emulsification of cataract lenses.

In the field of cataract lens eye surgery, many advances have taken place in the recent past to more efficiently remove the cataract lens from the eye. The cataract is a clouding of the lens of the eye which, over time, reduces the amount of light permitted to pass through the lens of the eye. Degeneration of the lens results in loss of sight in the eye and thus, the cataract must be removed and if opaque, the lens must be removed in total.

During the current advances of cataract lens removal, a plurality of hand-held instrumentalities were developed to assist in removing the cataract lens from the eye. Many of the instruments developed included finely controlled edges employed for cutting, scraping or puncturing the cataract lens for removing the opaque section blocking the passage of light. A more recent advance employs the use of emulsification which incorporates a high frequency ultrasonic source within the hand-held instrument for converting the electrical energy delivered to the ultrasonic source to a high frequency mechanically vibrating tip or cone.

The tip or cone of the ultrasonic instrument included one of a plurality of edges which was surrounded by a cylindrical sleeve or jacket which carried a sterile saline solution for irrigating the operative site within the lens of the eye. By physically touching the cataract lens of the human eye with the high frequency vibrating ultrasonic hand-held instrument, the hardened opaque cataract lens was emulsified and reduced to a liquid state. As the eye was irrigated with the saline solution, the emulsified debris of the destroyed cataract lens was vacuumed away by a low pressure suction from inside the hollow center of the tip or cone of the hand-held ultrasonic instrument. The saline solution and the emulsified debris were then disposed of through a channel connected to the end of the ultrasonic cone.

The hand-held instrumentality must be in physical contact with the lens of the eye in order for the ultrasonic sound waves to emulsify the fragments of the cataract lens within the eye. Therefore, the patient is normally under local anesthetic.

Various ultrasonic hand-held instrumentalities employed to emulsify the cataract lens of the human eye by applying a tip or cone directly to the cataract lens have been known for a number of years, and by way of example, several forms of such devices can be found in U.S. Pat. Nos. 4,515,583; 4,609,368; and 4,589,415.

The ultrasonic driver unit of each of the prior hand-held instrumentalities vibrated at a very high frequency. By way of example, a typical vibration frequency was 40 kHz. However, frequency ranges of (40 to 60) kHz are now available. The higher frequency ranges provide for a more rapid emulsification of the cataract lens leading to a shorter operable time for the patient.

In general, the instruments have included an outer housing comprised of an ultrasonic aspirator having the ultrasonic driver unit housed therein. The driver unit is linked to an operable probe or ultrasonic cone which is employed for making physical contact with the cataract lens. The driver unit is connected to the cone by a plurality of linkage designed to transmit the mechanical vibrations of the driver unit to the ultrasonic cone.

Typically, the ultrasonic aspirator housing further includes a cooling system designed to carry away heat generated by the frictional force of the ultrasonic cone and the driver unit. Also, the aspirator includes a fluid duct system for delivering the irrigating saline solution to the annular sleeve that surrounds the ultrasonic cone. The proximal end of the ultrasonic cone is typically threaded and is received by a female threaded horn permanently connected to the linkage between the driver unit and the cone.

The cone typically has a flange located forward of the cone threads and a hub that is employed for threading the cone into the horn with a mechanical instrument, for example, such as a wrench. The hub typically measures a larger dimension than that of the shaft of the ultrasonic cone, and it is the reduction of the dimension from the hub to the cone shaft that has been the subject of a major problem in the past.

Under prolonged use of the hand-held ultrasonic instruments, erosion of the material located between the hub and the shaft of the ultrasonic cone occurs. This erosion of the ultrasonic cone occurs in the interface where the radius makes a transition between the hub and the shaft of the cone. The ultrasonic mechanical vibrations travel up and down the shaft of the cone and across the transition radius of curvature which blends the hub to the shaft of the cone. The mechanical vibrations will strike the quasi-vertical portion of the radius interface resulting in mechanical damage and erosion of the ultrasonic cone in the region of the transition radius. Further, for a particular ultrasonic cone having a fixed transition radius, ultrasonic vibrations at a higher frequency or vibrations accompanied by a greater horizontal stroke will result in increased erosion.

The ultrasonic cone is typically comprised material which is neutral and non-chemically reactive with the human body, by way of example, such as titanium. Thus, if a portion of the titanium cone was to erode into flakes and fall into the human eye, then the human body would not build up an antibody resistance to the titanium and cause an infection impairing vision as would occur with other foreign substances.

The titanium cone erodes because the ultrasonic device sends the high frequency vibrations up and down the cone shaft. It is well known that the ultrasonic frequency is inversely proportional to the angle of incidence of the transition radius. The ultrasonic frequency of vibration is in most cases the determining factor, and for a fixed angle of incidence of the transition radius, higher ultrasonic frequencies result in increased erosion. Therefore, in the (40 to 60) kHz range of ultrasonic vibrations, visible particles of matter will erode from the ultrasonic cone which is evidenced by microscopic photographs of the cone after prolonged use.

Generally, as the ultrasonic frequency increases, the erosion of the ultrasonic cone further increases. As an example, experiments were conducted with an ultrasonic instrument employing an angle of incidence of 75 degrees and frequencies in the range of (40 to 60) kHz. Under these conditions, erosion was extremely excessive, resulting in substantial reduced life of the ultrasonic cone.

Another condition that will result in the erosion of the ultrasonic cone along the radius of curvature is the stroke of the shaft of the cone. The stroke of the cone shaft is most easily visualized as the back-and-forth horizontal vibration along the length dimension of the cone shaft. In the past, the horizontal stroke of the cone shaft was in the range of two-to-three thousandths of an inch but later was increased to the range of four-to-five thousandths of an inch. Although the increased stroke length improved the efficiency and speed of the aspirator in emulsifying a cataract lens, the erosion of the cone along the transition radius further reduced the useful life of the cone. Future designs anticipate increasing the horizontal stroke of the cone to the range of ten thousandths of an inch. Thus, increasing the vibration frequency or stroke of the cone having a fixed angle of incidence results in increased erosion of the cone.

Several attempts in the past to solve these problems have met with limited success. Any mechanical scores, scratches, or tool lines on the surface of the transition radius was an obvious site for erosion to occur. The scores, scratches and tool lines were potential stress points or stress-risers. The transition radius was necessary to blend the hub into the cone or shaft of the instrument. It was necessary to machine the outer surface of the transition radius to provide a smooth surface for reducing the likelihood of fracture. A first attempt to solve the erosion problem was to polish the surface where the erosion occurs. Therefore, any locations on the transition radius which included scores, scratches, or tool lines were polished in an effort to limit the erosion. However, the erosion continued to occur at frequencies greater than forty kilohertz.

Additional attempts to eliminate the erosion problem occurred during the manufacturing process of the ultrasonic cone. The first was acid etching of the entire ultrasonic cone which would remove any loose particulate matter or residue from the previous machining process. The acid etching reduced the ultrasonic cone to bare virgin metal.

The next manufacturing process included electro-polishing which is the opposite of electroplating. The process of electropolishing removes material from the surface of the ultrasonic cone which included particulate matter and residue from the previous machining process. In each of the manufacturing processes of acid etching and electropolishing, erosion continued to occur in the transition radius at frequencies greater than 40 kHz.

Other methods to prevent the erosion have also been attempted, one of which included providing a tapered transition in the region between the hub and the shaft of the ultrasonic cone, as is described, by way of example, in U.S. Pat. No. 3,589,363. Because erosion always occurred between the hub and the shaft along the transition radius of the ultrasonic cone, removal of that portion of the radius subject to erosion during manufacturing would eliminate the problem. However, if the erosion area was physically removed, the resulting surface would be too small in diameter to accommodate an installation tool normally employed to install the cone.

Therefore, the design of the transition radius was modified by construction methods for blending the material along the transition radius from the hub to the shaft. An example of such a method included constructing a line at a predetermined angle with the centerline of the shaft of the ultrasonic cone. Then, a radius of curvature was randomly selected so that the curve was tangent to the constructed line and the horizontal. Next, a line was constructed from the center of the curve to be perpendicular to an empirically determined point of tangency on the curve. Although a transition radius could be designed in this manner, an erosion area continued to exist substantially shortening the useful life of the cone.

A further construction technique which failed to solve the problem called for constructing a line at a specific angle and tangent to a corner of the hub. Then, a pair of vertical lines were drawn orthogonal to the constructed line. The constructed line was then bisected between the points of intersection of the two vertical lines and a third vertical line was drawn orthogonal to the constructed line at the bisection point and parallel to the pair of vertical lines. A fourth line was drawn perpendicular to the intersection point of the second of the pair of vertical lines on the shaft. Then, the fourth line was extended upward to intersect the third vertical line for establishing the center of an arc of the transition radius of curvature. However, the resulting transition radius failed to eliminate the erosion areas located along the quasi-vertical surfaces of the ultrasonic cone.

During the operation of the hand-held ultrasonic instrument, if the angle of incidence from the hub to the shaft of the ultrasonic cone is very large (for example, such as 75 degrees), the mechanical vibrations against the saline solution (cavitation) caused by increasing the frequency of vibration and the length of the stroke result in the formation of large bubbles along the transition radius. The large bubbles travel down the shaft of the ultrasonic cone and enter the eye at the site of the emulsification process impeding the view of the surgeon. To counteract this problem, a tube must be placed at the site of the emulsification process for vacuuming the large bubbles away from the surgical site.

Hence, those concerned with the development and use of hand-held ultrasonic instruments for the removal of cataract lens have long recognized the need for improved ultrasonic cones which reduce the erosion of the metal of the cone along the transition radius and also which reduce the cavitation and creation of bubbles along the transition radius to extend the life of the instrument and to reduce the visual impediments to the surgeon, respectively. The present invention fulfills all of these needs.

SUMMARY OF THE PRESENT INVENTION

Briefly, and in general terms, the present invention provides a hand-held ultrasonic cone construction which substantially reduces the amount of erosion of the material comprising the ultrasonic cone along the transition radius which blends the material of the square hub to the shaft for extending the life of the ultrasonic cone, and which substantially reduces the size of air bubbles formed within the operative site of the human eye caused by the cavitation of the cone within the sterile saline solution. Moreover, the cone construction of the present invention extends the range of the ultrasonic frequencies available for emulsification of the cataract lens, extends the useful life of the cone and permits reducing the angle of incidence from the square hub to the shaft as the ultrasonic frequency of vibration is increased.

Basically, the present invention is directed to an improved ultrasonic cone and method of construction for mounting in an ultrasonic aspirator which provides high frequency ultrasonic waves for removing the opaque section of a cataract lens by emulsification techniques.

The ultrasonic cone is comprised of a hub portion which is blended into a tapered shaft portion which is hollow and includes a generally beveled edge at the distal end. The cone is threadedly inserted into an ultrasonic horn with the cone having a flange located at the rear end of the hub which acts as a limit stop and mechanically secures the cone to the horn.

The tapered shaft is surrounded by a sleeve which provides an annular space between the sleeve and the cone. The annular space acts as a channel for the passage of a sterile saline solution to the operative site while the hollow portion of the shaft acts as a vacuum inlet permitting the saline solution and the emulsified debris of the cataract lens to be vacuumed therethrough. The distal end of the tapered shaft extends beyond the end of the sleeve permitting physical contact with the eye of the patient.

The angle formed between the horizontal and a constructed line passing through the circumference of the flange at the corner of the square hub and which intersects the tapered shaft of the cone is defined as the angle of incidence. It is known that the angle of incidence is inversely proportional to the ultrasonic frequency of the hand-held aspirator. In general, if the ultrasonic frequency of vibration of the cone increases then the angle of incidence must decrease in order to minimize the erosion of the ultrasonic cone along the transition radius.

In order to minimize the erosion of the cone along the transition radius, for frequencies greater than 40 kHz, the angle of incidence must be limited to 30 degrees or less. As the ultrasonic frequency of vibration increases or as the horizontal stroke of the cone shaft increases, the speed of the emulsification process increases, reducing the operative time. However, as the frequency or horizontal stroke increases, the design size of the angle of incidence must be reduced in order to minimize the erosion of the ultrasonic cone.

In accordance with the improved method of the present invention, a geometric method is disclosed for determining the transition radius of curvature for an angle of incidence of 30 degrees and an ultrasonic vibration frequency greater than 40 kHz. Alternative embodiments add an economical feature by introducing a disposable ultrasonic cone shaft and a plurality of emulsifying and cutting distal ends for improving the utility of the apparatus.

The new and improved ultrasonic cone of the present invention minimizes the erosion of the cone along the transition region by employing an angle of incidence designed to eliminate the destruction of the quasi-vertical portions of the hub by the mechanical vibrations traveling up and down the tapered shaft. By reducing the erosion, the useful life of the ultrasonic cone is extended many times over, which permits the cone to accommodate higher ultrasonic frequencies which increase the efficiency of the hand-held ultrasonic aspirator. By reducing the angle of incidence along the transition radius, the size of bubbles created by cavitation between the vibrating ultrasonic cone and the saline solution are reduced eliminating the need to disperse such bubbles in the operative site of the human eye by a separate apparatus. Further, by introducing a disposable cone shaft, the ultrasonic cone becomes more economical to fabricate. Also a selection of distal ends of the shaft portion are available increasing the utility of the device.

These and other objects and advantages of the invention will become apparent from the following more detailed description, when taken in conjunction with the accompanying drawings of illustrative embodiments.

DETAILED DESCRIPTION OF THE PREFERRED EMBODIMENT

As shown in the drawings for purposes of illustration, the invention is embodied in an ultrasonic cone 20 of the type employed in cataract lens eye surgery and mounted within a hand-held ultrasonic aspirator 10 and having a transition radius of curvature 22 blending the material of the cone 20 from a hub portion 24 to a shaft portion 26, the transition radius being determined by a geometric method for reducing the erosion of the metal along the transition radius during high frequency vibration.

Figure 1:
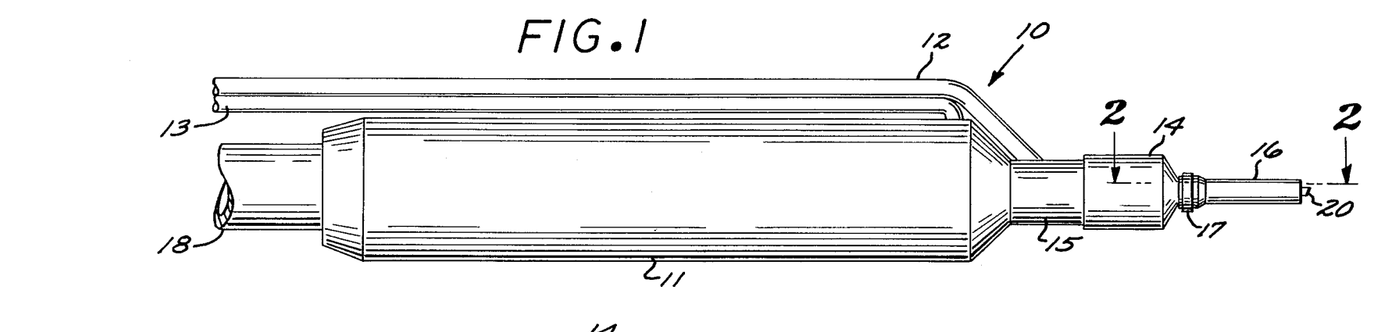
FIG. 1 is a side elevation view of a hand-held ultrasonic aspirator of the prior art.

The aspirator 10 is an apparatus which has been commonly employed to house a high frequency ultrasonic source, a debris vacuuming system, and the mechanical support for the ultrasonic cone 20, as shown in FIG. 1. The aspirator 10 further comprises a housing 11, a fluid inlet tube 12, a fluid outlet tube 13, a fluid housing 14, a hollow body portion 15, a hollow removable sleeve member 16, a sleeve retaining clip 17, a channel duct 18, and the tip of the ultrasonic cone 20 extending from the sleeve member 16.

The ultrasonic source (shown best in FIG. 2) acts as a transducer converting the electrical energy to the high frequency mechanical vibrations. The mechanical vibrations are transmitted through connective linkage to the cone 20 for providing the ultrasonic wave utilized for the emulsification of the cataract lens. The fluid inlet tube 12 provides an inlet path for operative fluids such as a sterile solution employed for flushing the operative site in the human eye. Also, the sterile solution acts to collect the emulsified debris for flushing away from the operative site.

The hollow removable sleeve member 16 surrounding the tip of the cone 20 provides an annular space for drawing the emulsified debris and spent saline solution therethrough for evacuating the site of the surgery. The vacuumed waste is drawn through the fluid outlet tube 13 which passes through the hollow body portion 15, into the main housing 11 and evacuated therefrom. The channel duct 18 further includes a fluid cooling system (not shown) for carrying away the excessive heat created by the high frequency ultrasonic source.

After prolonged use of the hand-held ultrasonic aspirator 10, erosion of the material located between the hub portion and the shaft portion occurs. This erosion of the ultrasonic cone occurs at the interface where the radius makes a transition between the hub and the shaft of the cone. The ultrasonic mechanical vibrations travel along the shaft of the cone and across the transition radius of curvature which blends the hub to the shaft of the cone. The traveling mechanical vibrations result in damage to and erosion of the cone in the region of the transition radius.

Additionally, for a particular cone having a fixed transition radius, ultrasonic vibrations at higher frequencies or a greater horizontal stroke result in increased erosion. This is because the frequency of vibration of the cone is inversely proportional to the angle of incidence of the transition radius. Therefore, for a fixed angle of incidence of the transition radius, higher ultrasonic frequencies or a greater horizontal stroke result in increased erosion. This problem is vividly illustrated in the (40-60) KHz frequency range in which visible particles of matter erode from the cone.

A first attempt to solve this erosion problem was to polish the surface at the location of scratches, scores or tool lines where the erosion occurs. Also, acid etching and electropolishing were each employed during the manufacturing process to remove any loose flakes and smooth the exterior surface. Another method included providing a tapered transition in the region between the hub and the shaft of the cone. Notwithstanding, erosion continued to occur in the region of the transition radius at frequencies greater than forty kilohertz. Even physical removal of the portion of the transition radius subject to erosion was not satisfactory since an inadequate hub portion remained for installation. Construction methods to modify the transition radius were also unsuccessful as discussed hereinafter.

An additional problem resulted where the angle of incidence from the hub to the shaft of the ultrasonic cone was large, for example, seventy-five degrees or more. The mechanical vibrations against the saline solution resulted in the formation of large bubbles along the transition radius. This cavitation resulted in the large bubbles traveling down the shaft of the cone and entering the eye at the site of the emulsification process. The bubbles impeded the view of the surgeon and required the presence of an auxiliary vacuuming tube.

In accordance with the present invention, the hub portion 24 and the shaft portion 26 of the cone 20 cooperate to reduce the erosion of the material along the transition radius 22 during high frequency mechanical vibrations by maintaining the angle of incidence $\theta$ equal to or less than thirty degrees and to significantly decrease the size of large bubbles formed along the transitional radius caused by the cavitation between the vibrating shaft and the saline solution. Further, the cone 20 eliminates the need for an additional device for disposing of the bubbles and improves the direct view of the operative site, substantially extends the life of the ultrasonic cone, permits the accommodation of higher frequency vibrations, reduces the time for emulsifying the cataract lens, and increases the efficiency of the process.

The angle of incidence $\theta$ is formed between a horizontal line and a constructed line passing through the circumference of a flange 34 and intersecting the shaft portion 26 as described hereinafter and shown in FIG. 6. The proximal end of the cone 20 includes a threaded portion 28 which threadedly engages a horn 30 extending from an ultrasonic driver unit 32. The horn 30 includes a plurality of inner threads which engage the threaded portion 28 for mechanically securing the cone 20 to the driver unit 32, as shown in FIG. 2.

Forward of the threaded portion 28 toward a distal end 35 of the cone 20, is the flange 34 which abuts against the horn 30 when the cone is threadedly inserted. The flange 34 assists in holding the cone 20 in alignment with the driver unit 32 and helps make the cone mechanically secure to the horn 30 for transmitting the high frequency ultrasonic waves to the distal end 35 of the cone 20.

Figure 2:
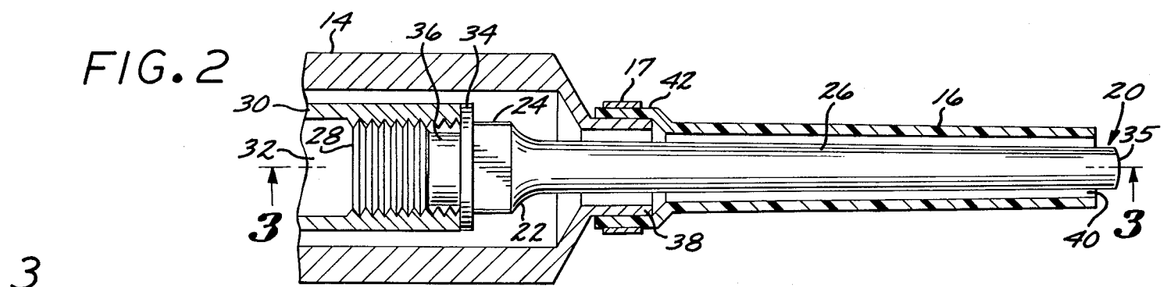
FIG. 2 is a cross-sectional view of an ultrasonic cone in accordance with the present invention and taken along line 2—2 of FIG. 1.
Figure 3:
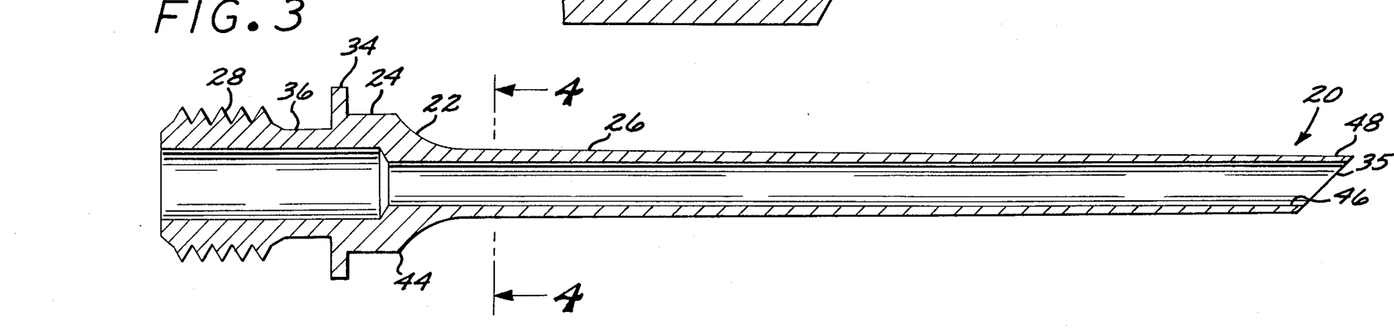
FIG. 3 is a cross-sectional view of the ultrasonic cone taken along line 3—3 of FIG. 2.

Between the threaded portion 28 and the flange 34 is a thread relief portion 36 which is visible in each of FIGS. 2 and 3. The thread relief 36 permits the cutting of a final thread of the threaded portion 28 while simultaneously permitting the creation of the flange 34 for providing abutment support against the horn 30. If the thread relief 36 were not present, the threaded portion 28 would taper off and the flange 34 could not otherwise be formed to abut against the horn. Therefore, the thread relief 36 is important in the formation of the flange 34.

The cone 20 is inserted into the horn 30 by rotating the cone in the direction which engages the threaded portion to the cone. The rotation of the cone 20 is achieved by mechanically rotating the hub portion 24 with an appropriate tool. The hub portion, also known as a "wrench pad", may include any one of a plurality of geometric configurations such as a square, a hexagonal, or other appropriate design. The hub portion or wrench pad may be captured in the jaws of a tool, such as a wrench, for mechanically inserting into or withdrawing from the threaded portion of the horn. Typically, the wrench is comprised of a plastic material for preventing damage to the cone.

The shaft portion 26 is generally tapered, as shown in FIG. 3, to provide stability and strength to the cone. A shaft having a uniform thickness would be unsuitable since the distal end 35 of the cone 20 would be too large for the nimble contact with the eyeball that is necessary. Further, a uniform thickness would provide inadequate support at the proximal driven end of the cone 20 resulting in instability of the cone.

Note that the distal end 35 of the cone 20 is shown beveled in FIG. 3, however, a variety of shapes of the distal end are available. By way of example, such shapes may include cones having distal ends that are square, round, irregular in shape, in addition to being beveled. A plurality of beveled angles are available, depending upon the application of the cone 20, with examples of such angles being within the range of 15 to 30 degrees, 37½ degrees, 45 degrees, and 60 degrees. Other designs include 60-degree beveled angles branching out to yet further angles. Thus, the wall thickness of the cone 20 varies because of the taper of the shaft portion 26. For example, the distal end of the cone contacting the operative site is thinner while the proximal end of the tapered shaft is thicker for providing support at the driven end of the cone.

The fluid housing 14 surrounds the horn 30 and the proximal end of the cone 20 as shown in FIG. 2. The forward end of the fluid housing tapers forming an annular portion 38 which surrounds the cone 20 and maintains the structural integrity of an annular duct 40 formed between the sleeve member 16 and the shaft portion 26. The sleeve member 16 is tapered and permits the distal end 35 of the cone 20 to extend beyond the terminal end of the sleeve. The proximal end of the sleeve forms a circular mounting portion 42 which is annular in nature and receives the annular portion 38 of the fluid housing 14 in a concentric manner. The sleeve retaining clip 17 retains the circular mounting portion 42 about the annular portion 38 as shown in FIG. 2.

The transition radius 22 accommodates the change in diameter between the tapered shaft 26 and the hub portion 24. The radius is designed in such a manner as to minimize the erosion and flaking of the metal comprising the cone 20 during mechanical vibrations equal to and exceeding 40 kHz. During the high frequency vibrations, the ultrasonic waves travel up and down the shaft 26 and are deflected by the quasi-vertical structure or skirt formed in the transition radius 22 when passing from the shaft to the hub portion.

Figure 6:
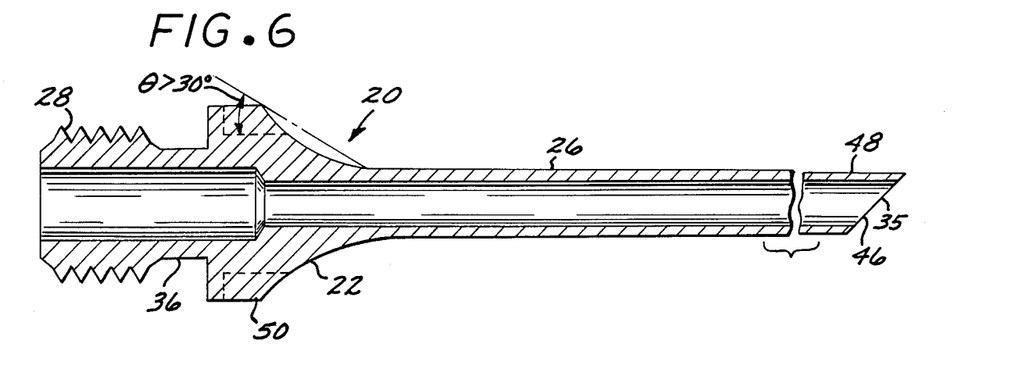
FIG. 6 is a cross-sectional view of the ultrasonic cone illustrating the construction of the angle of incidence and the area of erosion.
Figure 8:
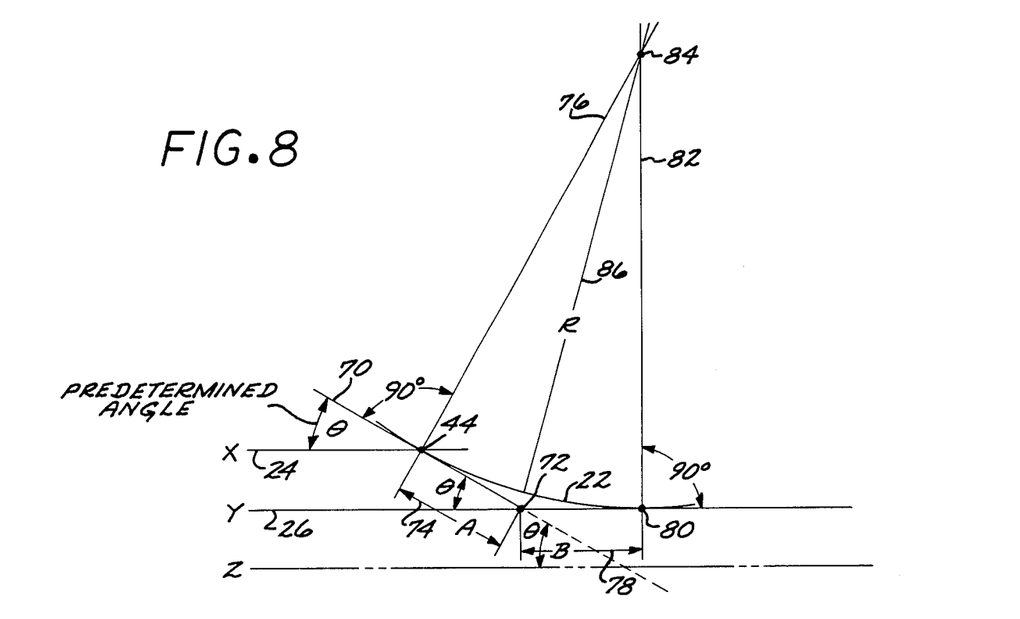
FIG. 8 is an enlarged fragmentary portion of the ultrasonic cone illustrating the method of geometric construction for determining the transition radius of curvature in accordance with the present invention.

The proper radius of curvature for the transition radius 22 may be determined geometrically if the angle of incidence, as illustrated in FIGS. 6 and 8, is equal to or less than 30 degrees. This provides a radius of curvature which experiences the minimum erosion practically attainable for a specified ultrasonic vibration frequency. The method for determining the proper radius of curvature will be described hereinafter in conjunction with FIG. 8. Also note that the cone 20 is illustrated as being hollow throughout the shaft portion 26 which permits the removal of the emulsified debris and spent saline solution therethrough.

The cone 20 is normally comprised of a titanium alloy since this material is generally inert when in contact with the human body. Therefore, during the emulsification process, if flakes of the titanium alloy fall into the operative site of the human eye, infection and potential permanent damage to the eye will not occur. Other substitute materials are also available since certain varieties of stainless steel are also inert and do not chemically react with the human body. The determination of which material the cone may be comprised of is controlled by the appropriate government agencies.

Generally, the appropriate mathematical relationship is that the angle of incidence $\theta$ of the transition radius 22 in relation to the direction of stroke in ultrasonic equipment is in inverse relationship to the frequency of the ultrasonic force applied and is illustrated in Equation (1) below.

$$\text{Angle of Incidence } (\theta) \approx 1/f \quad (1)$$

By inspection of Equation (1), it is evident that if the ultrasonic frequency became infinite, the angle of incidence $\theta$ would be very small (approximately 5 degrees) and the transition radius would be very long. Therefore, in the limit, a problem would exist in that the hand-held ultrasonic instrument would become too heavy because the long transition radius would require additional metal. The current frequency range extends up to 60 kHz which permits the cone 20 to be sufficiently lightweight for practical use in the human eye.

Figure 4:
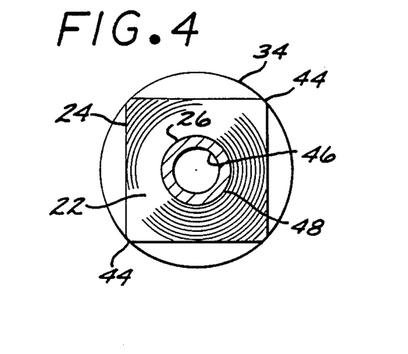
FIG. 4 is a cross-sectional view of the transition radius of the tapered shaft taken along line 4—4 of FIG. 3.

The transition radius 22 may be viewed looking from the direction of the distal end 35 of the shaft portion 26, as is illustrated in FIG. 4. The hub portion 24 is shown superimposed upon the flange 34 with each of the four corners of the hub being identified as a point 44, as is further illustrated in FIG. 3. Further, the inner and outer diameters 46, 48 of the shaft 26, respectively, are shown centered over the hub portion 24. The inner and the outer diameters 46, 48 are also shown in FIGS. 3 and 6.

Figure 5:
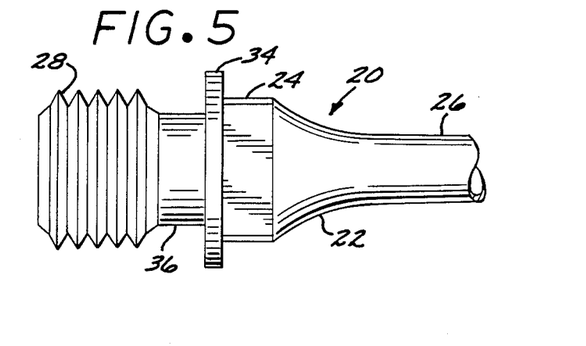
FIG. 5 is an enlarged side elevational view of the ultrasonic cone of FIG. 2.

The proximal end of the shaft portion 26 and the transition radius of curvature 22 are fashioned in a circular nature permitting the shaft portion to blend into the hub portion 24 as is shown in FIG. 5. Further, the threaded portion 28 is shown completing a final thread and tapering down to the smaller diameter of the thread relief 36 permitting the formation of the flange 34. As can be seen, the hub portion 24 adjacent the flange 34 is an ideal location to position the wrench pad for driving the threaded portion into and out of the horn 30 shown in FIG. 2.

The length of the transition radius 22 is a direct result of the angle of incidence $\theta$. The problem of erosion of the material along the transition radius 22 exists because the angle of incidence, by design, causes the ultrasonic forces of vibration to be deflected from the quasi-vertical portion of the transition radius. When the ultrasonic frequency or the horizontal stroke is increased, the angle of incidence $\theta$ determines the magnitude of the reflected mechanical vibrations traveling along the shaft portion 26. In the case in which the angle of incidence is larger than 30 degrees and the ultrasonic frequency of vibration exceeds 40 kHz, the erosion section 50 (shown in phantom in FIG. 6) will disintegrate. Under these conditions, the life of the ultrasonic cone 20 is limited by the upper range of the ultrasonic frequency employed in the aspirator 10. Since the angle of incidence $\theta$ is fixed during the design of the cone 20, the upper boundary of the ultrasonic frequency and the length of the horizontal stroke employed is the limiting factor.

In the instant invention, the peak ultrasonic frequency and the maximum horizontal stroke to be employed are factors to be considered when determining the angle of incidence $\theta$. For a peak ultrasonic frequency of vibration exceeding 40 kHz or a horizontal stroke greater than four-thousandths of an inch, the angle of incidence must be less than or equal to 30 degrees. When the ultrasonic frequency or the horizontal stroke is increased, the angle of incidence is made smaller leaving less metal along the quasi-vertical portion of the transition radius 22 to be eroded away.

For any particular ultrasonic frequency or horizontal stroke to be employed, the angle of incidence $\theta$ is determined by empirical observation by monitoring the wear on the cone 20 over an extended period of time at particular test frequencies. Under these conditions, a particular angle of incidence $\theta$ may be adopted which is sufficiently small for a particular frequency of vibration or horizontal stroke.

By way of example, test results indicated that erosion was excessive in the quasi-vertical section of the transition radius 22 when the design angle of incidence is greater than 30 degrees for an ultrasonic vibration frequency of 50 kHz. However, under the same test conditions at the same frequency, erosion of the cone 20 was radically reduced when the design angle of incidence was 30 degrees.

Geometric construction techniques have been employed in the past to arrive at the optimum transition radius of curvature 22. Empirical evidence of erosion collected from microscopic photographs indicates that certain areas along the transition radius do erode at high vibration frequencies and long horizontal strokes while other areas do not erode. Obviously, the solutions based upon geometric construction have progressed from the data collected from additional photographs of the transition radius after the construction solution was instituted.

A key element in the development of a suitable geometric construction has been the location at which the erosion begins. This location would appear along the interface between the area which does erode and the area which does not erode. Knowledge of the location of where the erosion begins assists in locating the point of tangency of the arc along the transition radius 22. As the shaft portion 26 begins to sweep upwards upon entering the transition radius, the erosion area is encountered and the correct angle of incidence $\theta$ is necessary to minimize the erosion.

Generally, construction techniques have focused upon blending the transition radius 22 from the shaft portion 26 to the hub portion 24. Normally, a line was constructed at a specified angle with the horizontal centerline of the shaft portion. Then a circle having the correct radius, which was measured as with a protractor, was selected. The circumference of the circle was positioned so as to be tangent to the construction line and to the shaft portion centerline. Then a separate line was drawn so as to be orthogonal to the arc of the circle at the point at which the erosion begins as indicated by the photographs. However, an erosion area continued to exist along the transition radius above the point of tangency.

Figure 7:
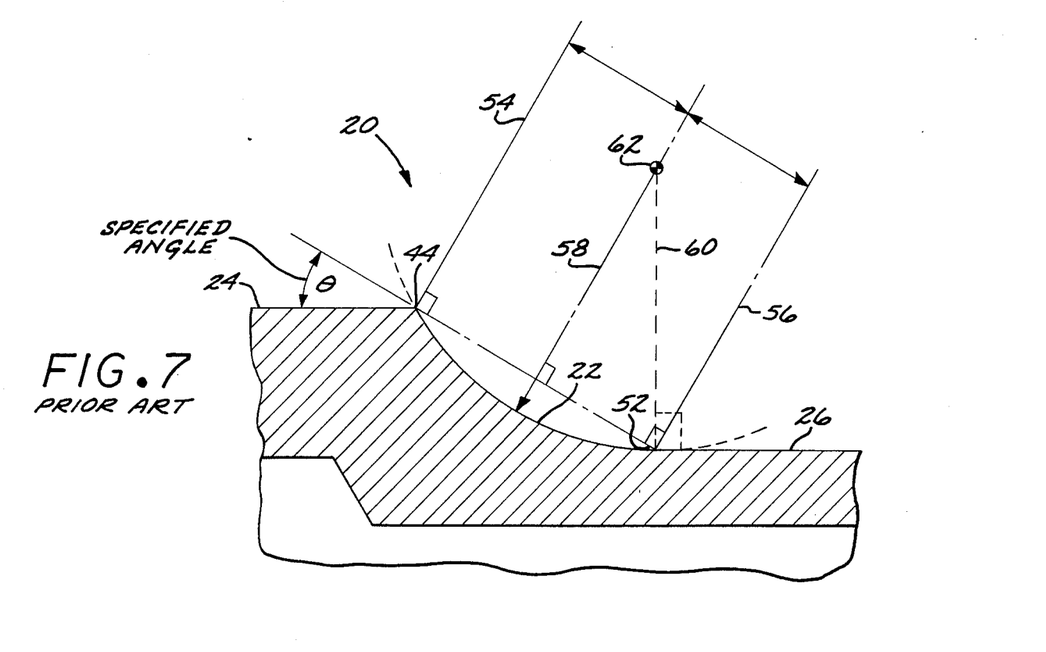
FIG. 7 is an enlarged fragmentary portion of a cross-sectional view of the ultrasonic cone illustrating the method of geometric construction for determining the transition radius of curvature in the prior art.

Construction methods for designing a transition radius 22 having a specified range for the angle of incidence $\theta$ at an ultrasonic vibration frequency of greater than forty kilohertz have been incorporated into the manufacturing process but have failed to eliminate the erosion. A line was constructed at an angle within the specified range which was tangent to hub corner 44 with the end of the constructed line intersecting the shaft portion 26 at point 52 as shown in FIG. 7. The hub corner was positioned on the circumference of flange 34 so that the location of point 44 was controlled by the hub corner. However, the location of point 52 was controlled by the constructed line at the angle of incidence $\theta$.

Then a pair of vertical lines 54, 56 were drawn perpendicular to the constructed line. The first vertical line 54 intersected the constructed line at the hub corner 44 while the second vertical line 56 intersected the constructed line at point 52. The constructed line was then bisected between the points of intersection 44, 52 of the lines 54, 56 and a third line 58 was drawn parallel to lines 54, 56 and orthogonal to the constructed line at the bisection point. A fourth line 60 was then drawn perpendicular to point 52 on the shaft portion 26 and was thereafter extended upward intersecting line 58 at point 62. Point 62 established the center of an arc having a radius equivalent to line 60 for constructing a transition radius. Notwithstanding, this construction technique also failed to eliminate the erosion areas at vibration frequencies greater than forty kilohertz.

One of the many objectives of the instant invention is to eliminate the erosion section 50 located along the transition radius 22 as is illustrated in FIG. 6. It has been determined that the erosion section 50 can be eliminated if the transition radius is increased. If the transition radius is increased, a position will be reached at which the point of tangency with the center of the transition radius will form an incident angle $\theta$ of less than or equal to thirty degrees with the centerline of the ultrasonic shaft portion 26.

The erosion section 50 can be eliminated by relocating the point of tangency with the center of the transition radius 22 to the square hub corner 44 as is illustrated in FIG. 8. Further, relocation of the point of tangency with the center of the transition radius is accomplished by increasing the size of the arc of the circle along the transition radius. Various construction techniques have been developed to permit the size of the arc along the transition radius to be increased. By way of example, the following construction technique is disclosed for accomplishing this goal.

A line 70 should be constructed so that the angle $\theta$ formed between the line 70 and the hub portion 24 (represented by the line "X") at the hub corner 44 is less than or equal to thirty degrees. The size of the angle $\theta$ formed by the constructed line 70 is a function of the operation vibration frequency selected. The exterior surface of the shaft portion 26 (represented by the line "Y") is parallel to the hub portion 24 (represented by line "X"). Since the centerline of the shaft portion 26 (represented by the line "Z") is parallel to both the exterior surface of shaft portion 26 and to the hub portion 24 (Line X), the angles formed between the line 70 and the lines ("Y" and "Z") are also equal to $\theta$. This determination is based on the geometric relationship of the equivalency of alternate interior angles of parallel lines. Because of the position of line 70, the point 44 and a point 72 are respectively fixed at the intersection of line 70 with lines "X" and "Y".

A distance 74 located between point 44 and point 72 is determined to be "A" units. At point 44, construct a line 76 which is orthogonal to line 70 and extend the line 76 upward. Next, measure a distance 78 located between the point 72 (where line 70 intersects the line "Y") and a point 80 (located on line "Y") to be "B" units. The construction should provide that line 74 having the distance of "A" units is equivalent in length to line 78 having the distance of "B" units.

Now a line 82 should be constructed at point 80 which is orthogonal to the line "Y" and the line "Z" along the centerline of the shaft portion 26. Extend the line 82 upward to intersect with the line 76 for locating the center 84 of a circle. Finally, construct a radius 86 (designated by the line "R") from the center of the circle 84 to the point 44 which becomes the point of tangency. The radius 86 may be rotated about the center 84 from the point of tangency 44 to the point 80 for constructing the transition radius 22. By employing this construction, the erosion section 50 will be eliminated if the angle of incidence $\theta$ is made smaller than thirty degrees as the vibration frequency of the ultrasonic aspirator 10 is increased. The size of the angle of incidence is $\theta$ presently determined by empirical observation.

In designing an ultrasonic cone 20 to be employed in an aspirator operated at an ultrasonic frequency greater than 40 kHz, the above-described method should be utilized to determine the appropriate radius of curvature after the angle of incidence has been empirically determined. If the angle of incidence $\theta$ is reduced as the ultrasonic frequency increases, the erosion and damage caused by the mechanical vibration striking the quasi-vertical portion of the transition radius will be minimized.

If the angle of incidence $\theta$ is very large (for example, seventy-five degrees), large bubbles are formed by cavitation. Bubbles are formed because of the mechanical vibration of the cone 20 against the saline solution which surrounds the ultrasonic cone in the annular duct 40. The large bubbles formed in the saline solution are created along the transition radius 22 and travel along the shaft portion 26 to the distal end 35 of the cone and into the operative site.

Although reducing the angle of incidence $\theta$ does not eliminate the bubble formation along the transition radius 22, the bubbles that are formed are smaller and are easier to disperse at the operative site. Thus cavitation is prevented and the large bubbles are eliminated. If the bubbles are large, a special irrigation and aspiration tip must be employed to disperse the large bubbles during the emulsification procedure.

An advantage is that the smaller bubbles do not require a special irrigation and aspiration tube for dispersion as the finely divided aeration allows the small bubbles to be reabsorbed into the fluids of the eye. However, the emulsification debris in the eye must still be removed through the hollow tip of the cone 20. After the emulsification of the cataract lens, the saline solution not only acts as a vehicle for carrying away the emulsified debris but also acts as a coolant to eliminate the possibility of damage to the human eye caused by excessive heat at the distal end 35 of the cone 20.

Elimination of the erosion section 50 located along the transition radius 22 may also be accomplished by a first alternative embodiment of the ultrasonic cone referred to by the general reference character 120 and incorporating the present invention. In this instance, the first alternative embodiment of the cone 120 in FIGS. 9 through 10 also is of the high frequency type somewhat similar to the ultrasonic cone 20 of FIGS. 1 through 8. Parts of the cone 120 of FIGS. 9 through 10 which find substantial correspondence in structure and function to those parts of FIGS. 1 through 8 are designated with corresponding numerals of the one-hundred series.

Figure 9:
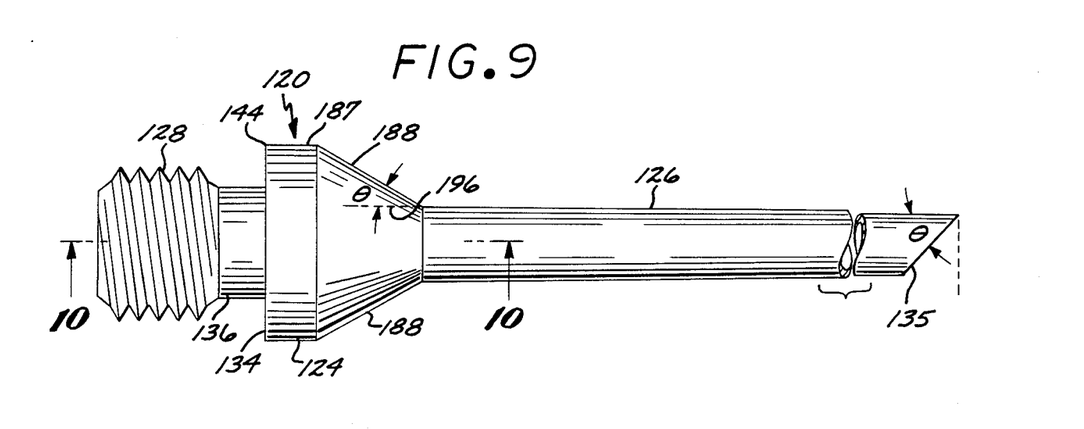
FIG. 9 is a side elevational view of a first alternative embodiment of an ultrasonic cone of the present invention.
Figure 10:
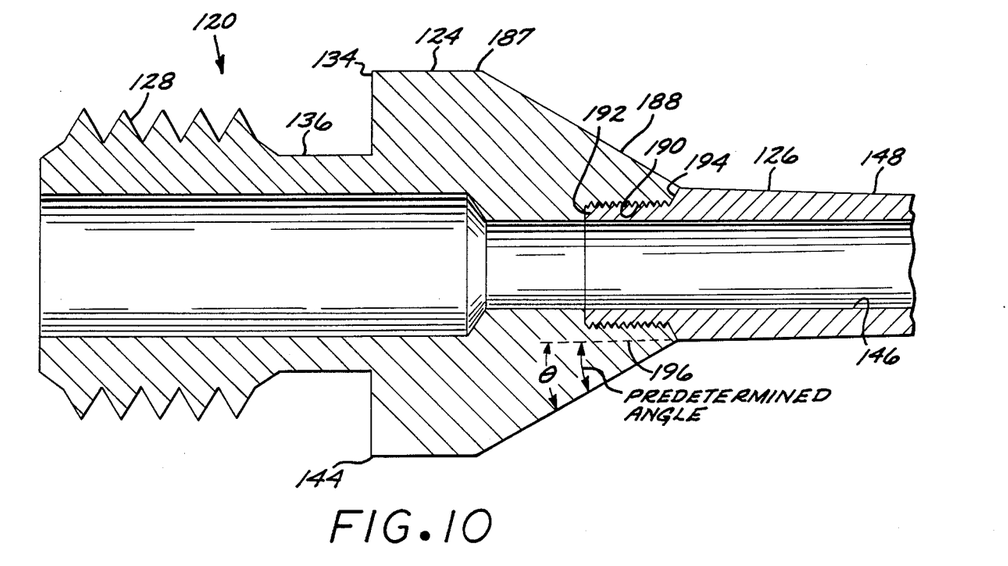
FIG. 10 is a cross-sectional view of the ultrasonic cone taken along the line 10—10 of FIG. 9.

The ultrasonic cone 120 is equipped with an adaptor 187 which acts as a coupler for locking a shaft portion 126 to the cone. The shaft portion can be locked to the cone by, for example, threading action as shown in FIGS. 9 and 10. The adapter 187 includes a hub portion 124 employed for installing and removing the cone from an ultrasonic aspirator 110. The hub portion interfaces with a tapered portion 188 of the adapter which is generally shaped as a conical frustum. The hub portion may have any of a plurality of shapes for serving as a wrench pad as previously noted in the preferred embodiment.

The ultrasonic cone 120 also includes a threaded portion 128 which permits the cone to be secured within a horn 130 surrounding an ultrasonic driver unit 132 similar to that shown in FIG. 1. The cone can be threaded into the horn until a flange 134 which acts as a limit stop is reached. The threaded portion 128 is separated from the flange 134 by a thread relief portion 136. The thread relief portion permits the final thread of the threaded portion 128 to be cut as described in reference to FIG. 5.

The elements comprising the ultrasonic aspirator 110 are also incorporated into the aspirator which employs the ultrasonic cone 120. These elements which are not shown in FIGS. 9 and 10 but correspond to the numbers of FIG. 1 include a housing 111, a fluid inlet tube 112, a fluid outlet tube 113, a fluid housing 114, a hollow body portion 115, a hollow removable sleeve member 116, a sleeve retaining clip 117 and a channel duct 118. Also included is a distal end 135 of the shaft portion 126, an annular portion 138, an annular duct 140 and a circular mounting portion 142. Finally, shown in FIGS. 9 and 10 is a square hub corner 144, a shaft inner diameter 146 and a shaft outer diameter 148.

The interior of the tapered portion 188 of the adapter 187 includes a plurality of threads 190 for receiving a threaded proximal end 192 of the shaft portion 126 as shown in FIG. 1. The threaded proximal end 192 has a smaller diameter than the shaft portion and has the threads cut on the outer surface of the proximal end. The mating threads 190 are cut on the inside of the tapered portion 188 of the adapter 187. The shaft portion 126 is tapered as in the preferred embodiment with the proximal end 192 having a larger diameter than the distal end 135. The shaft portion is hollow for accommodating the vacuum removal of debris floating in the operative site. An annular stop 194 located at the interface of the proximal end 192 and the shaft portion 126 acts as a limit stop.

By employing the adapter 187, a fully disposable shaft portion 126 is made possible. The shaft portion may be removed from the adapter in the following manner. The shaft portion can be gripped from the beveled distal end 135 by one of a plurality of special tools (not shown) comprised of plastic and designed so as to avoid damaging the exterior surface. The special tool may be configured as a set of fingers that grip the shaft portion by engulfing the beveled distal end. The figures may then be collapsed onto the shaft portion by applying pressure at a specified point on a compressive grip of the tool. Once the grip is released, the special tool will slide off of the shaft portion 126.

Another example of one of the plurality of special tools is a tool comprised of, for example, a flexible plastic and shaped in the form of a letter "C". The "C" tool might have extension ears formed at each end and displaced by ninety degrees from the gap in the "C". Then, two compressive studs are mounted perpendicular to the extension ears. The "C" tool can be mounted over the shaft portion 126 and pressure for rotating the shaft portion out of or into the adapter 187 may be applied by the compressive studs. In either case, the special tools may be fabricated as a disposable or a reusable item.

The adapter 187 includes an angle of incidence $\theta$ which is located between the tapered portion 188 of the adapter and a horizontal line 196 parallel to the centerline of the shaft portion 126. As in the preferred embodiment, the magnitude of the angle $\theta$ must be less than or equal to thirty degrees. If the angle $\theta$ is limited to the range prescribed, the erosion of the adapter and the shaft portion will be avoided when frequencies exceeding forty kilohertz and a horizontal stroke exceeding four-to-five thousandths of an inch are employed. As before, the angle of incidence $\theta$ must be reduced in size when the range of frequencies employed or the length of the horizontal stroke is increased. The angle of incidence $\theta$ is shown most clearly in FIG. 10. Because the tapered portion 188 has a fixed slope, a transition radius of curvature does not appear in the first alternative embodiment. The slope of the tapered portion may be machined to include the predetermined angle of incidence $\theta$ for the particular vibration frequency and length of horizontal stroke that will be employed by the cone 120.

The distal end 135 of the shaft portion 126 includes a beveled end which is available in various angles such as, for example 15°, 30°, 45° and 60° or any angle that may be desired. For all angle cuts less than 60°, the beveled distal end will tend to erode at frequencies greater than forty kilohertz and for horizontal stroke lengths greater than four-to-five thousandths of an inch for the same reasons as previously described. For angle cuts equal to or greater than 60°, erosion is virtually eliminated because the angle of incidence $\theta$ located at the beveled distal end is reduced to thirty degrees or less. Thus, the angle of incidence of the beveled distal end located between the exterior horizontal line of the shaft portion 126 and the cut angle is thirty degrees or less. The angle from the vertical line to the cut angle is sixty degrees or more as shown in FIG. 9.

Therefore, the adapter 187 and the cone 120 cooperate to eliminate the erosion of the material along the tapered portion 188 and the beveled distal end 135 at vibration frequencies exceeding forty kilohertz and horizontal stroke lengths exceeding four-to-five thousandths of an inch. Further, the adapter acts as a coupler permitting the shaft portion 126 of the cone to be completely disposable. Because the ultrasonic cones are expensive to fabricate, the disposable cone shaft portion provides a more economical solution being cheaper to replace. Further, since erosion is eliminated, the debris from the cone that floats into the operative site is also reduced.

Figure 11:
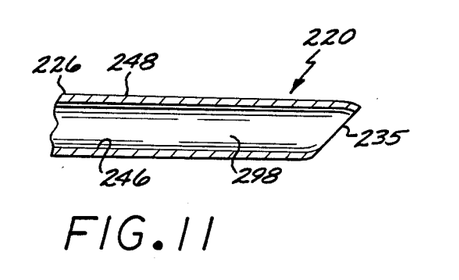
FIG. 11 is a partial side elevational view of a second alternative embodiment of an ultrasonic cone of the present invention.

Although the distal end 135 of the shaft portion 126 shown in FIG. 9 is designed with an angle of incidence of less than or equal to thirty degrees for minimizing erosion, modification of the distal end will result in more efficient emulsification of a cataract lens. The higher efficiency is achieved by introducing a second alternative embodiment of the ultrasonic cone referred to by the general reference character 220 and incorporating the present invention. In this instance, the second alternative embodiment of the cone 220 illustrated in FIG. 11 is also of the high frequency type somewhat similar to the ultrasonic cone 20 of FIGS. 1 through 8. Parts of the cone 220 of FIG. 11 which find substantial correspondence in structure and function to those parts of FIGS. 1 through 8 are designated with corresponding numerals of the two-hundred series.

The ultrasonic cone 220 is mounted in an ultrasonic aspirator as was described in the preferred embodiment. Those portions of the ultrasonic cone except for a distal end 235 is as described in the previous embodiments. However, note that the novel improvements of the ultrasonic cone 220 may be incorporated into the ultrasonic cone 20 which includes the transition radius of curvature 22 or the ultrasonic cone 120 which includes the adapter 187 with the tapered portion 188.

The cone 220 includes a shaft portion 226 having an inner diameter 246 and an outer diameter 248 terminating in the distal end 235. A channel 298 is accessible from the distal end and is employed to carry away the emulsified debris during the removal of the cataract lens. A common problem associated with emulsification of a cataract lens is the clogging of the channel 298 of the shaft portion 226 during the procedure. As the high frequency vibrations of the ultrasonic cone 220 liquify the opaque portion of the cataract lens, certain of the emulsified debris continues to exist in a semi- solid state. Because the inner diameter 246 of the shaft portion 226 is extremely small, the hollow portion may become clogged during the procedure.

Note that in addition to the distal end 235 being beveled, it is also somewhat constricted or compressed for acting as a screening entrance to the channel 298. Since the distal end 235 is somewhat constricted or compressed, the inner diameter 246 of the channel 298 is wider than the compressed distal end. The compressed distal end acts to block emulsified debris at the entrance of the channel 298 preventing the debris from entering the channel and blocking the shaft portion 226 beyond the distal end. Therefore, if a portion of the emulsified debris is capable of passing through the compressed distal end 235, it may be assured that the debris will pass through the channel 298 of the shaft portion 226 and into the fluid outlet tube of the ultrasonic aspirator as is shown in FIGS. 1 and 2.

Figure 12:
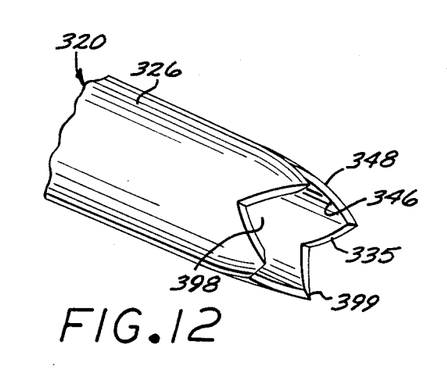
FIG. 12 is a partial perspective view of a third alternative embodiment of an ultrasonic cone of the present invention.
Figure 13:
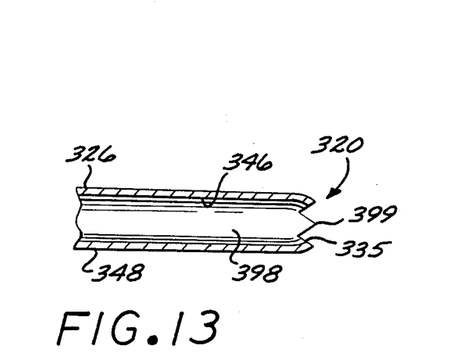
FIG. 13 is a partial side elevational view of the ultrasonic cone of FIG. 12.
Figure 14:
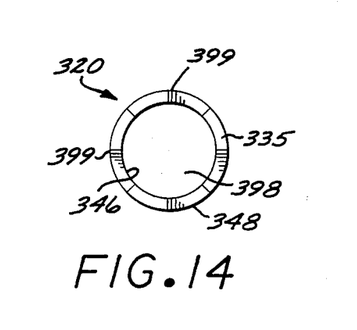
FIG. 14 is an enlarged front elevational view of the ultrasonic cone of FIG. 12.

Additional modifications of the ultrasonic cone will further improve the efficiency of the emulsification technique. The improved efficiency may be accomplished by a third alternative embodiment of the ultrasonic cone referred to by the general reference character 320 and incorporating the present invention. As before, the third alternative embodiment of the cone 320 illustrated in FIGS. 12 through 14 is also of the high frequency type very similar to the ultrasonic cones of the previous embodiments. Parts of the cone 320 of FIGS. 12 through 14 which find substantial correspondence in structure and function to those parts of the previous embodiments are designated with corresponding numerals of the 300 series.

The ultrasonic cone 320 is somewhat similar to the ultrasonic cones described in the previous embodiments and may be employed in the preferred embodiment incorporating the transition radius of curvature 22 or in the first alternative embodiment incorporating the adapter 187 having the tapered portion 188. The ultrasonic cone 320 includes a tapered shaft portion 326 having an inner diameter 346 and an outer diameter 348 forming a channel 398 and terminating in a distal end 335 as is shown in FIGS. 12 through 14.

In the previous embodiments, the distal end 335 was beveled at any one of a plurality of angles. An additional problem that continues to exist is that although the beveled end is designed to minimize erosion, only a single cutting edge exists. Therefore, during the emulsification procedure, the surgeon finds it necessary to rotate and manipulate the ultrasonic aspirator to permit contacting the entire cataract lens with the single cutting edge. The rotation and manipulation of the aspirator increases the probability of resulting damage to the eyeball.

The distal end 335 of the shaft portion 326 includes a plurality of cutting surfaces 399 as is shown in FIG. 12.

The cutting surfaces are formed as by milling or grinding the distal end 335 for creating the desired configuration. Although four cutting edges are shown in FIGS. 12 through 14, any configuration may be adopted which may be practically realized in the machining process. The addition of the plurality of cutting surfaces 399 dispenses with the requirement that the surgeon rotate and manipulate the aspirator during the emulsification procedure. Further, multiple cutting surfaces permit the surgeon to attack the cataract lens from multiple positions resulting in liquifying the lens in a more efficient manner.

The ultrasonic cone 320 also adopts the constricted or compressed distal end 335 as is clearly shown in FIG. 13. The compressed distal end 335 acts as a screening entrance to the channel 398 for eliminating blockage in the channel. The plurality of cutting surfaces 399 are also somewhat compressed inwardly for cooperating with the constricted distal end eliminating larger semi-solid debris particles which would otherwise clog the channel 398. If a debris particle is sufficiently small to pass the constricted distal end 335, then the particle will successfully pass through the channel 398 and on through the fluid outlet tube of the ultrasonic aspirator.

The distal end 335 of the ultrasonic cone 320 not only prevents residue debris from blocking the channel 398 but also employs the plurality of inwardly compressed cutting surfaces 399 for cutting away ocular shards. An ocular shard is a small fragmentary growth located within the eye and can be a long and continuous lense portion. In the alternative embodiment, the shard is removed by cutting rather than by employing emulsification techniques on the lenses. The cutting surfaces 399 are compressively turned down to restrict the front opening to the channel 398 and are angled at, for example, 45° so that each cutting surface acts as a cutting point.

The shards are cut and removed instantaneously minimizing the operative time and economizing on the use of the available ultrasonic energy. After removal by manipulating the ultrasonic cone 320, the shards are entrapped within the inwardly compressed cutting surfaces 399 and are directed through the channel 398 to tee fluid outlet tube of the ultrasonic aspirator. A major advantage of this feature is that most of the post removal clean-up of debris is eliminated.

From the foregoing, it will be appreciated that the ultrasonic cone 20 of the invention minimizes the erosion of the metal material along the transition radius 22 by selecting the proper angle of incidence $\theta$ for the design ultrasonic frequency and length of horizontal stroke to be employed. The employed design extends the useful life of the ultrasonic cone while the range of ultrasonic frequencies and the length of the horizontal stroke employed by the cone 20 is increased for improving the efficiency of the process by reducing the time required for emulsifying the cataract lens. Further, the inverse proportional relationship between the angle of incidence $\theta$ and the ultrasonic frequency of vibration permits the angle of incidence $\theta$ to be properly selected for the desired peak vibration frequency and horizontal stroke for each ultrasonic cone which reduces excessive erosion and minimizes the negative effects of the bubbles created by cavitation along the transition radius. Also, the ultrasonic cones of the alternative embodiments further add the desirable features of economy with the introduction of a disposable cone shaft and an array of distal ends available for improving the emulsifying and cutting efficiency of the ultrasonic cone.

While several particular forms of the invention have been illustrated and described, it will be apparent that various modifications can be made without departing from the spirit and scope of the invention. Accordingly, it is not intended that the invention be limited, except as by the appended claims.

What is claimed is:

1. An ultrasonic cone for the emulsification of a cataract lens comprising, in combination:
    fastening means for connecting said cone to an ultrasonic driver unit;
    securing means located adjacent said fastening means on said cone for mechanically aligning said cone to and securing said cone against a horn of said driver unit;
    a hub in mechanical communication with said securing means for facilitating the installation and removal of said cone from said horn;
    a shaft connected to said hub for transmitting a plurality of ultrasonic vibrations to a distal end of said shaft for mechanically communicating with and for emulsifying said cataract lens, said shaft being cylindrical; and
    a transition radius of curvature located intermediate said hub and said shaft for blending a sectional dimension of said hub with a sectional dimension of said shaft, said transition radius of curvature having an angle incidence no greater than 30° with said hub for eliminating structural erosion along said transition radius of curvature at vibration frequencies greater than forty kilohertz and for horizontal stroke lengths of said shaft exceeding the range of four-to-five thousandths of an inch.

2. The ultrasonic cone of claim 1 wherein said fastening means comprises a threaded portion located at a proximal end of said cone.

3. The ultrasonic cone of claim 1 wherein said securing means comprises a flange integral with said cone and abutting said driver unit.

4. The ultrasonic cone of claim 1 wherein said hub comprises a square hub for providing a wrench pad for rotating said cone.

5. The ultrasonic cone of claim 1 wherein said hub comprises a hex hub for providing a wrench pad for rotating said cone.

6. The ultrasonic cone of claim 1 wherein said shaft comprises a tapered shaft.

7. The ultrasonic cone of claim 1 wherein said shaft is hollow for providing a means for evacuating debris from said emulsified cataract lens.

8. The ultrasonic cone of claim 1 wherein said shaft is circular in cross-section.

9. The ultrasonic cone of claim 1 wherein said distal end of said shaft is beveled for improved cataract lens contact.

10. The ultrasonic cone of claim 1 wherein an inside diameter of said shaft distal end is smaller than an inside diameter of said shaft for limiting the size of a plurality of emulsified debris entering said distal end for preventing blockage within said shaft, said inside diameter of said shaft distal end being concave in shape.

11. The ultrasonic cone of claim 1 wherein said shaft distal end further includes a plurality of cutting surfaces for efficient removal of said cataract lens wherein said shaft distal end includes an inside diameter which is concave in shape.

12. The ultrasonic cone of claim 1 wherein said ultrasonic cone is comprised of a titanium alloy, said titanium alloy being inert with respect to said lens.

13. The ultrasonic cone of claim 1 wherein said ultrasonic cone is comprised of a stainless steel alloy, said stainless steel alloy being inert with respect to said lens.

14. The ultrasonic cone of claim 1 wherein said angle of incidence is less than 30° for vibration frequencies greater than fifty kilohertz.

15. The ultrasonic cone of claim I wherein said securing means seals a cavity within said horn from a plurality of fluids located within said ultrasonic driver unit.

16. An ultrasonic cone for the emulsification of a cataract lens comprising, in combination:
   a threaded portion for connecting said cone to an ultrasonic driver unit;
   a flange located adjacent said threaded portion on said cone for mechanically aligning said cone to and securing said cone against a horn of said driver unit;
   a wrench pad hub in mechanical communication with said flange for facilitating the installation and removal of said cone from said horn;
   a shaft connected to said wrench pad hub for transmitting a plurality of ultrasonic vibrations to a distal end of said shaft for mechanically communicating with and for emulsifying said cataract lens, said shaft being cylindrical; and
   a transition radius of curvature located intermediate said wrench pad hub and said shaft for blending a sectional dimension of said wrench pad hub with a sectional dimension of said shaft, said transition radius of curvature having an angle of incidence no greater than 30° with said hub for eliminating structural erosion along said transition radius of curvature at vibration frequencies greater than forty kilohertz and for horizontal stroke lengths of said shaft exceeding the range of four-to-five thousandths of an inch.

17. The ultrasonic cone of claim 16 wherein an inside diameter of said shaft distal end is smaller than an inside diameter of said shaft for limiting the size of a plurality of emulsified debris entering said distal end of preventing blockage within said shaft, said inside diameter of said shaft distal end being concave in shape.

18. The ultrasonic cone of claim 16 wherein said shaft distal end includes a plurality of cutting surfaces for efficient removal of said cataract lens and wherein the inside diameter of said distal end is concave in shape.

19. An ultrasonic cone for the emulsification of a cataract lens comprising, in combination:
   a threaded portion located at a proximal end of said cone for connecting said cone to an ultrasonic driver unit;
   a flange located adjacent said threaded portion on said cone, said flange for mechanically aligning said cone to and securing said cone against a horn of said driver unit and for sealing a cavity within said horn from a plurality of fluids located within said ultrasonic driver unit;
   a thread relief located intermediate said threaded portion and said flange, said thread relief for terminating a complete thread of said threaded portion permitting the formation of said flange;
   a wrench pad hub in mechanical communication with said flange for facilitating the installation and removal of said cone from said horn;
   a shaft connected to said wrench pad hub for transmitting a plurality of ultrasonic vibrations to a distal end of said shaft for mechanically communicating with and for emulsifying said cataract lens said shaft being cylindrical and wherein the inside diameter of said distal end is concave in shape; and
   a transition radius of curvature located intermediate said wrench pad hub and said shaft for blending a sectional dimension of said wrench pad hub with a sectional dimension of said shaft, said transition radius of curvature having an angle of incidence no greater than 30° with said hub for eliminating structural erosion along said transition radius of curvature for vibration frequencies greater than forty kilohertz and for horizontal stroke lengths of the shaft exceeding the range of four-to-five thousandths of an inch.

20. An ultrasonic cone for the emulsification of a cataract lens comprising, in combination:
   a threaded portion located at a proximal end of said cone for connecting said cone to an ultrasonic driver unit;
   a flange located adjacent said threaded portion on said cone for mechanically aligning said cone to and securing said cone against a horn of said driver unit;
   a hub in mechanical communication with said flange for facilitating the installation and removal of said cone from said horn;
   a shaft connected to said hub for transmitting a plurality of ultrasonic vibrations to a distal end of said shaft for mechanically communicating with and for emulsifying said cataract lens, said shaft having a plurality of threads located at a proximal end of said shaft; and
   an adapter located intermediate said hub and said shaft for providing a tapered portion for transition from a sectional dimension of said hub to a sectional dimension of said shaft, said tapered portion of said adapter having an angle of incidence no greater than thirty degrees for eliminating structural erosion along said adapter at vibration frequencies greater than forty kilohertz and for horizontal stroke lengths of said shaft exceeding the range of four-to-five thousandths of an inch, said adapter including a threaded cavity for receiving said threaded proximal end of said shaft.

21. The ultrasonic cone of claim 20 wherein an inside diameter of said shaft distal end is smaller than an inside diameter of shaft for limiting the size of a plurality of emulsified debris entering said distal end for preventing blockage within said shaft, said inside diameter of said distal end being concave in shape.

22. The ultrasonic cone of claim 20 wherein said shaft distal end includes a plurality of cutting surfaces for efficient removal of said cataract lens, said inside diameter of said distal end being concave in shape.

23. An ultrasonic cone for the removal of a cataract lens comprising, in combination:
   a threaded portion located at a proximal end of said cone for connecting said cone to an ultrasonic driver unit;
   a flange located adjacent said threaded portion on said cone for mechanically aligning said cone to and securing said cone against a horn of said driver unit;

a hub in mechanical communication with said flange for facilitating the installation and removal of said cone from said horn;

a shaft connected to said hub for transmitting a plurality of ultrasonic vibrations to a distal end of said shaft for mechanically communicating with said cataract lens, said shaft distal end including a plurality of cutting surfaces for severing a plurality of fragmentary shards connected to said cataract lens, said shaft being cylindrical; and a transition radius of curvature located intermediate said hub and said shaft for blending a sectional dimension of said hub with a sectional dimension of said shaft, said transition radius of curvature having an angle of incidence no greater than 30° with said hub for eliminating structural erosion along said transition radius of curvature at vibration frequencies greater than forty kilohertz and for horizontal stroke lengths of said shaft exceeding the range of four-to-five thousandths of an inch.

24. An ultrasonic cone for the removal of a cataract lens comprising, in combination:

a flange located adjacent said threaded portion on said cone for mechanically aligning said cone to and securing said cone against a horn of said driver unit;

a hub in mechanical communication with said flange for facilitating the installation and removal of said cone from said horn;

a shaft connected to said hub for transmitting a plurality of ultrasonic vibrations to a distal end of said shaft for mechanically communicating with said cataract lens, said shaft distal end having a concave shaped inside diameter and including a plurality of cutting surfaces for severing a plurality of fragmentary shards connected to said cataract lens; and an adapter located intermediate said hub and said shaft for providing a tapered portion for transition from a sectional dimension of said hub to a sectional dimension of said shaft, said tapered portion of said adapter having an angle of incidence no greater than 3° for eliminating structural erosion along said adapter at vibration frequencies greater than forty kilohertz and for horizontal stroke lengths of said shaft exceeding the range of four-to-five thousandths of an inch.

25. A method for constructing a transition radius of curvature of an ultrasonic cone for eliminating structural erosion of said cone, said method comprising the steps of:

defining a line at an angle less than or equal to 30° with a horizontal surface of a shaft portion, said constructed line intersecting a corner of a hub on said ultrasonic cone;

determining a first distance, said first distance being measured along said constructed line between said corner of said hub and said shaft portion;

erecting a first perpendicular line orthogonal to said corner of said hub for locating a number one point on said radius of curvature;

measuring a second distance equivalent to said first distance, said second distance being located along said shaft portion between an end of said first distance and a second point;

erecting a second perpendicular line orthogonal to said second point for locating a number two point on said radius of curvature;

extending said first and second perpendicular lines for forming a vertical intersection, said intersection for locating a center of a circle;

constructing a radius of said circle, said radius being equivalent in length to said first and second perpendicular lines, said first perpendicular line being measured between said center of said circle and said number one point and said second perpendicular line being measured between said center of said circle and said number two point;

rotating said radius along an arc for forming said radius of curvature between said number one point and said number two point with a point of tangency being located at said corner of said hub; and forming a transition radius of curvature in said ultrasonic cone between said hub and said shaft portion for complying with said radius of said circle.

26. An ultrasonic cone for the emulsification of a cataract lens comprising, in combination:

fastening means for connecting said cone to an ultrasonic driver;

securing means located adjacent said fastening means on said cone for mechanically aligning said cone to and securing said cone against a horn of said driver unit;

relieving means formed on said cone intermediate said fastening means and said securing means for permitting the complete formation of said fastening means and said securing means;

a hub in mechanical communication with said securing means for facilitating the installation and removal of said cone from said horn;

a shaft connected to said hub for transmitting a plurality of ultrasonic vibrations to a distal end of said shaft for mechanically communicating with and for emulsifying said cataract lens, said shaft being cylindrical and having an inside diameter larger than the inside diameter of said distal end, said inside diameter of said distal end being concave in shape; and a transition radius of curvature located intermediate said hub and said shaft for blending a sectional dimension of said hub with a sectional dimension of said shaft, said transition radius of curvature having an angle of incidence no greater than 30° with said hub for eliminating structural erosion along said transition radius of curvature at vibration frequencies greater than forty kilohertz and for horizontal stroke lengths of said shaft exceeding the range of four-to-five thousandths of an inch.

27. An ultrasonic cone for the removal of a cataract lens comprising, in combination:

a threaded portion located at a proximal end of said cone for connecting said cone to an ultrasonic driver unit;

a flange located adjacent said threaded portion on said cone for mechanically aligning said cone to and securing said cone against a horn of said driver unit;

a thread relief formed on said cone intermediate said threaded portion and said flange for permitting the complete formation of said threaded portion and said flange;

a hub in mechanical communication with said flange for facilitating the installation and removal of said cone from said horn;

a shaft connected to said hub for transmitting a plurality of ultrasonic vibrations to a distal end of said shaft for mechanically communicating with said cataract lens, said shaft distal end including a plurality of cutting surfaces for severing a plurality of fragmentary shards connected to said cataract lens, said shaft being cylindrical and having an inside diameter larger than the inside diameter of said distal end, said inside diameter of said distal end being concave in shape; and a transition radius of curvature located intermediate said hub and said shaft for blending a sectional dimension of said hub with a sectional dimension of said shaft, said transition radius of curvature having an angle of incidence no greater than 30° with said hub for eliminating structural erosion along said transition radius of curvature at vibration frequencies greater than forty kilohertz and for horizontal stroke lengths of said shaft exceeding the range of four-to-five thousandths of an inch.

* * * * *